US00PP32524P2

(12) United States Plant Patent
Keogh

(10) Patent No.: US PP32,524 P2
(45) Date of Patent: Nov. 24, 2020

(54) ***PHILODENDRON* PLANT NAMED 'SHANGRI-LA'**

(50) Latin Name: *Philodendron bippinatifidum*
Varietal Denomination: SHANGRI-LA

(71) Applicant: Terence Charles Keogh, Victoria Point (AU)

(72) Inventor: Terence Charles Keogh, Victoria Point (AU)

( * ) Notice: Subject to any disclaimer, the term of this patent is extended or adjusted under 35 U.S.C. 154(b) by 0 days.

(21) Appl. No.: 16/602,939

(22) Filed: Dec. 27, 2019

(51) Int. Cl.
*A01H 5/00* (2018.01)

(52) U.S. Cl.
USPC ..... Plt./381

(58) Field of Classification Search
USPC ..... Plt./381
See application file for complete search history.

*Primary Examiner* — Annette H Para
(74) *Attorney, Agent, or Firm* — Cassandra Bright

(57) ABSTRACT

A new and distinct *Philodendron* cultivar named 'SHANGRI-LA' is disclosed, characterized by deeply lobed foliage and short, compact plants with abundant basal stems. The new variety is a *Philodendron*, normally produced as an indoor ornamental container plant.

1 Drawing Sheet

Latin name of the genus and species: *Philodendron bippinatifidum.*

Variety denomination: 'SHANGRI-LA'.

BACKGROUND OF THE INVENTION

The new *Philodendron* cultivar is a product of a planned breeding program conducted by the inventor at a research nursery in Queensland, Australia. The new variety was selected during 2015 at a research nursery in Queensland, Australia.

During 2014 seed was collected from an unnamed, unpatented proprietary *Philodendron bippinatifidum*. The pollen parent cannot be identified as seed was the result of an open-pollination with several *Philodendron bippinatifidum* present. The new variety was selected from the resultant seedlings based on the compact habit observed.

First asexual reproduction of the new cultivar 'SHANGRI-LA' was performed by vegetative terminal cuttings in 2015, and subsequently by tissue culture. First propagation occurred at the same research nursery in Queensland, Australia. Multiple generations have been produced, and have shown that the unique features of this cultivar are stable and reproduced true to type in successive generations.

SUMMARY OF THE INVENTION

The cultivar 'SHANGRI-LA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SHANGRI-LA' These characteristics in combination distinguish 'SHANGRI-LA' as a new and distinct *Philodendron* cultivar:

1. Short and compact plant habit.
2. Multiple basal stems.
3. Deeply lobed leaf blades with maturity.

PARENT COMPARISON

Plants of the new cultivar 'SHANGRI-LA' are comparable to the seed parent variety in most horticultural characteristics however, the new variety 'SHANGRI-LA' differs in the following:

1. The new variety is significantly shorter than the parent variety.
2. The new variety produces multiple main stems, the parent variety produces one to three main stems.

COMMERCIAL COMPARISON

Plants of the new cultivar 'SHANGRI-LA' are comparable to the variety *Philodendron hybridum* 'Little Hope', U.S. Plant Pat. No. 26,282. The two *Philodendron* varieties are similar in most horticultural characteristics however, the new variety 'SHANGRI-LA' differs in the following:

1. Mature height of the new variety is taller than the mature height of 'Little Hope'. The new variety is a short variety, while 'Little Hope' is a very short variety.
2. The new variety is a fuller, denser plant than 'Little Hope', producing more main stems.

Plants of the new cultivar 'SHANGRI-LA' are comparable to the commercial variety *Philodendron hybridum* 'Hope', unpatented. The two *Philodendron* varieties are similar in most horticultural characteristics, however the new variety differs in the following:

1. Mature height of the new variety is shorter than the mature height of 'Hope'. The new variety is a short variety, while 'Hope' is a medium height variety.
2. The new variety is a fuller, denser plant than 'Hope', producing more main stems.

BRIEF DESCRIPTION OF THE PHOTOGRAPH

The accompanying photograph illustrates in full color a plant of 'Shangri-La' in a 25 cm pot, approximately 8 months old from a single rooted tissue culture plantlet. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'SHANGRI-LA' plants grown in a climate controlled greenhouse in Melbourne, Australia. Temperatures ranged from 5° C. to 15° C. at night to 18° C. to 40° C. during the day. No artificial light, photoperiodic treatments were given to the plants. Measurements and numerical values represent averages of typical plant types.

Botanical classification: *Philodendron bippinatifidum* 'SHANGRI-LA'.

Propagation:

*Time to initiate roots*.—About 30 to 50 days at approximately 23° C.

*Root description*.—Fleshy, medium-thick, roots covered in fine lateral roots. Colored near RHS White 155A.

Plant:

*Age of the plant described*.—Approximately 9 months from a single rooted tissue culture plantlet, planted in a 25 cm pot.

*Growth habit*.—Compact, upright habit; freely branching from the base; very dense habit, vigorous growth; leave attitude upright, ageing to arching.

*Height*.—Approximately 40 cm.

*Plant spread*.—Approximately 60 cm.

*Growth rate*.—Rapid.

*Branching characteristics*.—Approximately 7 to 16 basal stems.

*Length of stem*.—11 cm.

*Diameter of stem*.—1.3 cm.

*Characteristics of stem*.—Form: Round. Color: Near RHS Yellow-Green 146C. Texture: Glabrous. Strength: Very strong.

Foliage:

*Arrangement*.—Alternate to whorled.

*Average length*.—Approximately 27 cm.

*Average width*.—Approximately 27 cm at widest point.

*General description*.—Highly lobed, overall oblate. immature leaves entire ageing to deeply divided.

*Shape of blade*.—Pinnatipartite.

*Apex*.—Apiculate.

*Base*.—Hastate.

*Margin*.—Immature entire, mature deeply sinuate.

*Appearance of top surface*.—Smooth, glabrous, glossy.

*Appearance of bottom surface*.—Smooth, glabrous, dull to medium glossy.

*Pubescence*.—Absent.

*Aspect*.—Slightly upwardly cupped.

*Color*.—Young foliage upper side: Near RHS Green 137B. Young foliage under side: Near RHS Yellow-Green 146A. Mature foliage upper side: Near RHS Green 137B. Mature foliage under side: Near RHS Yellow-Green 146A.

*Venation*.—Type: Pinnate. Venation color upper side: Near RHS Yellow-Green 146B. Venation color under side: Near RHS Yellow-Green 145A.

*Petiole*.—Average Length: Approximately 40 cm. Average Width: Approximately 1.4 cm. Color: Near RHS Yellow-Green 146C. Texture: Smooth.

Flower: Flowering has not been observed.

Other characteristics:

*Disease/pest resistance*.—Neither resistance nor susceptibility to pathogens and pests common to *Philodendron* have been observed.

*Temperature tolerance*.—The new variety tolerates temperatures between 0 to 45° C.

*Fruit/seed production*.—Not observed.

What is claimed is:

1. A new and distinct cultivar of *Philodendron* plant named 'SHANGRI-LA' as herein illustrated and described.

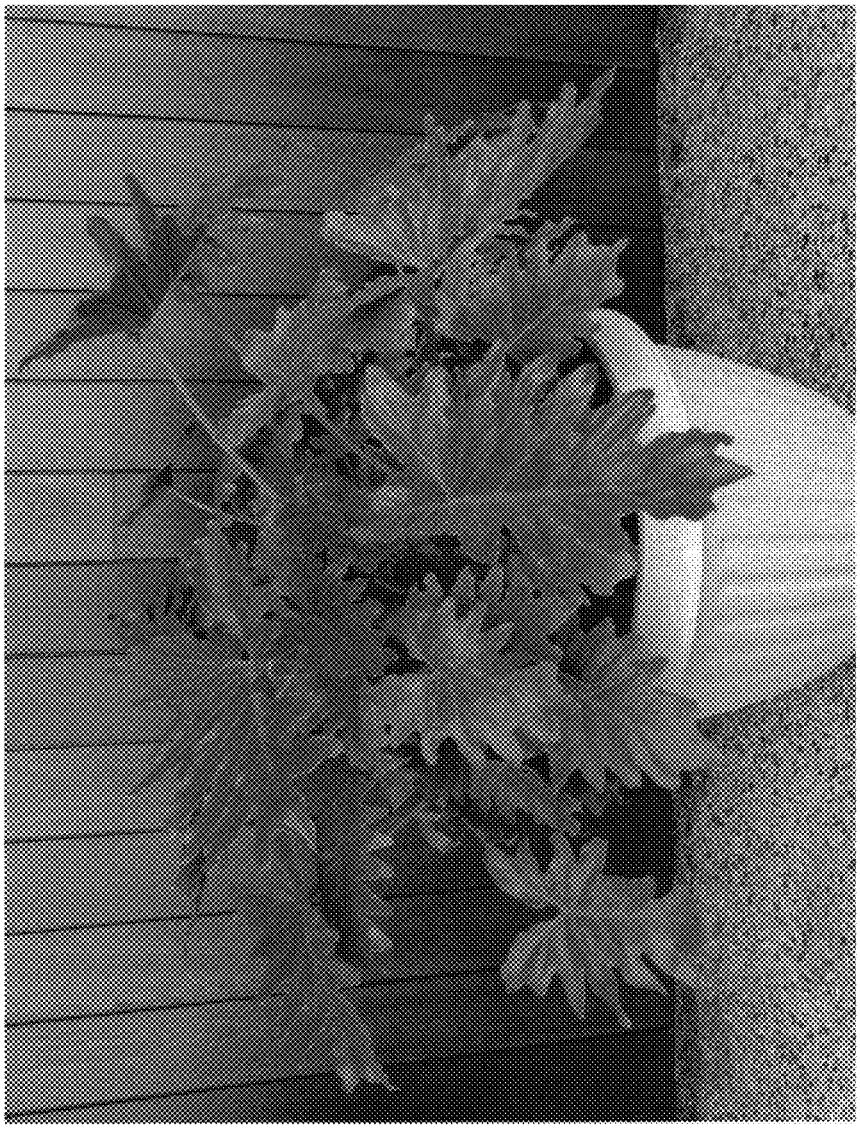

* * * * *